(12) United States Patent
Steininger (10) Patent No.: US 10,299,764 B2
(45) Date of Patent: May 28, 2019

(54) METHOD AND SYSTEM FOR ENHANCED VISUALIZATION OF MOVING STRUCTURES WITH CROSS-PLANE ULTRASOUND IMAGES

(71) Applicant: General Electric Company, Schenectady, NY (US)

(72) Inventor: Josef Steininger, Zipf (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 8 days.

(21) Appl. No.: 15/591,371

(22) Filed: May 10, 2017

(65) Prior Publication Data
US 2018/0325496 A1    Nov. 15, 2018

(51) Int. Cl.
*A61B 8/00* (2006.01)
*A61B 8/08* (2006.01)
(Continued)

(52) U.S. Cl.
CPC ............ *A61B 8/5246* (2013.01); *A61B 8/145* (2013.01); *A61B 8/4444* (2013.01); *A61B 8/4494* (2013.01); *A61B 8/463* (2013.01); *A61B 8/467* (2013.01); *A61B 8/469* (2013.01); *A61B 8/523* (2013.01); *B06B 1/0622* (2013.01); *G06T 7/246* (2017.01); *G06T 11/60* (2013.01); *G06T 19/00* (2013.01); *G06T 2207/10136* (2013.01); *G06T 2207/30196* (2013.01); *G06T 2207/30204* (2013.01); *G06T 2210/41* (2013.01); *G06T 2219/008* (2013.01); *G06T 2219/028* (2013.01)

(58) Field of Classification Search
None
See application file for complete search history.

(56) References Cited

U.S. PATENT DOCUMENTS 8,539,838 B2 * 9/2013 Yoo ..................... G01S 7/52065
                                                              600/443
8,798,342 B2    8/2014 Perrey et al.
(Continued)

FOREIGN PATENT DOCUMENTS

WO    WO 2015068073 A1 *  5/2015  ............. A61B 8/145

*Primary Examiner* — Michael J Cobb
(74) *Attorney, Agent, or Firm* — McAndrews, Held & Malloy, Ltd.; Jacob Groethe; David Bates (57) ABSTRACT

An ultrasound probe may continuously acquire a first cross-plane image and a second cross-plane image. The second cross-plane image may intersect the first cross-plane image at a cross-plane intersection line of the first-cross plane image. A processor may receive a selection of a reference position in the first cross-plane image along the cross-plane intersection line of the first cross-plane image. The reference position may correspond with at least a portion of a structure in the first cross-plane image. The processor may track movement of the selected reference position in the first cross-plane image over time. The processor may update an image acquisition position parameter of the second cross-plane image based on the tracked reference position such that the second cross-plane image intersects the first cross-plane image at the tracked reference position. A display system may continuously and simultaneously present the acquired first cross-plane image and the acquired second-cross plane image.

11 Claims, 6 Drawing Sheets

(51) Int. Cl.
*A61B 8/14* (2006.01)
*G06T 19/00* (2011.01)
*B60B 1/06* (2006.01)
*G06T 7/246* (2017.01)
*G06T 11/60* (2006.01)
*B06B 1/06* (2006.01)

(56) References Cited

U.S. PATENT DOCUMENTS

| | | | | |
|---|---|---|---|---|
| 2011/0079083 | A1* | 4/2011 | Yoo | G01S 7/52065 73/632 |
| 2012/0288172 | A1* | 11/2012 | Perrey | A61B 8/145 382/131 |
| 2015/0245819 | A1* | 9/2015 | Yoshiara | A61B 8/06 600/424 |
| 2015/0257739 | A1* | 9/2015 | Yao | A61B 8/06 600/431 |
| 2016/0000408 | A1* | 1/2016 | Matsunaga | A61B 8/06 600/441 |
| 2016/0367221 | A1* | 12/2016 | Igarashi | A61B 8/5207 |
| 2017/0164931 | A1* | 6/2017 | Ng | A61B 8/0841 |

* cited by examiner

METHOD AND SYSTEM FOR ENHANCED VISUALIZATION OF MOVING STRUCTURES WITH CROSS-PLANE ULTRASOUND IMAGES

FIELD

Certain embodiments relate to ultrasound imaging. More specifically, certain embodiments relate to a method and system for enhanced visualization of moving structures with cross-plane two-dimensional ultrasound images by tracking a position of structure in a first cross-plane image and updating the position of a second cross-plane image based on the tracked position of the structure in the first cross-plane image.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Ultrasound imaging may be helpful in viewing moving structures, such as tissue, medical instruments, and the like, in a region of interest over time. For example, a two dimensional array probe may be used to ultrasonically scan multiple planes of a volumetric region of interest simultaneously in real time. The two dimensional array enables beams to be transmitted and focused electronically through the volumetric region opposing the array transducer in two or more image planes in the region to simultaneously generate real-time images of each of the image planes. The imaging mode that simultaneously provides perpendicular two-dimensional imaging planes is referred to as a "biplane" or "cross-plane" mode. The cross-plane mode, which allows an organ to be imaged from perpendicular viewpoints at the same time, may provide enhanced viewing and tracking of an imaged structure. However, motion artifacts caused by the breadth of the imaged subject, movement of structure within the subject, and the like, may make analysis of the moving structure difficult and tedious. For example, an ultrasound operator may have to manipulate a trackball or move the ultrasound probe to change the position of the acquired perpendicular B-plane image each time a viewed structure in the A-plane image moves.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for enhanced visualization of moving structures with cross-plane two-dimensional ultrasound images, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for providing enhanced visualization of moving structures with cross-plane two-dimensional ultrasound images. For example, various aspects have the technical effect of enhancing visualization of a structure by tracking a position of the structure in a first cross-plane image and updating the position of a second cross-plane image based on the tracked position of the structure in the first cross-plane image.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present disclosure. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an exemplary embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the disclosure, such as single or multi-core: CPU, Graphics Board, DSP, FPGA, ASIC or a combination thereof.

Moreover, although certain embodiments in the foregoing description may describe analyzing a fetal heart, for example, unless so claimed, the scope of various aspects of the present disclosure should not be limited to a fetal heart and may additionally and/or alternatively be applicable to any suitable imaged structure having a changing position.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
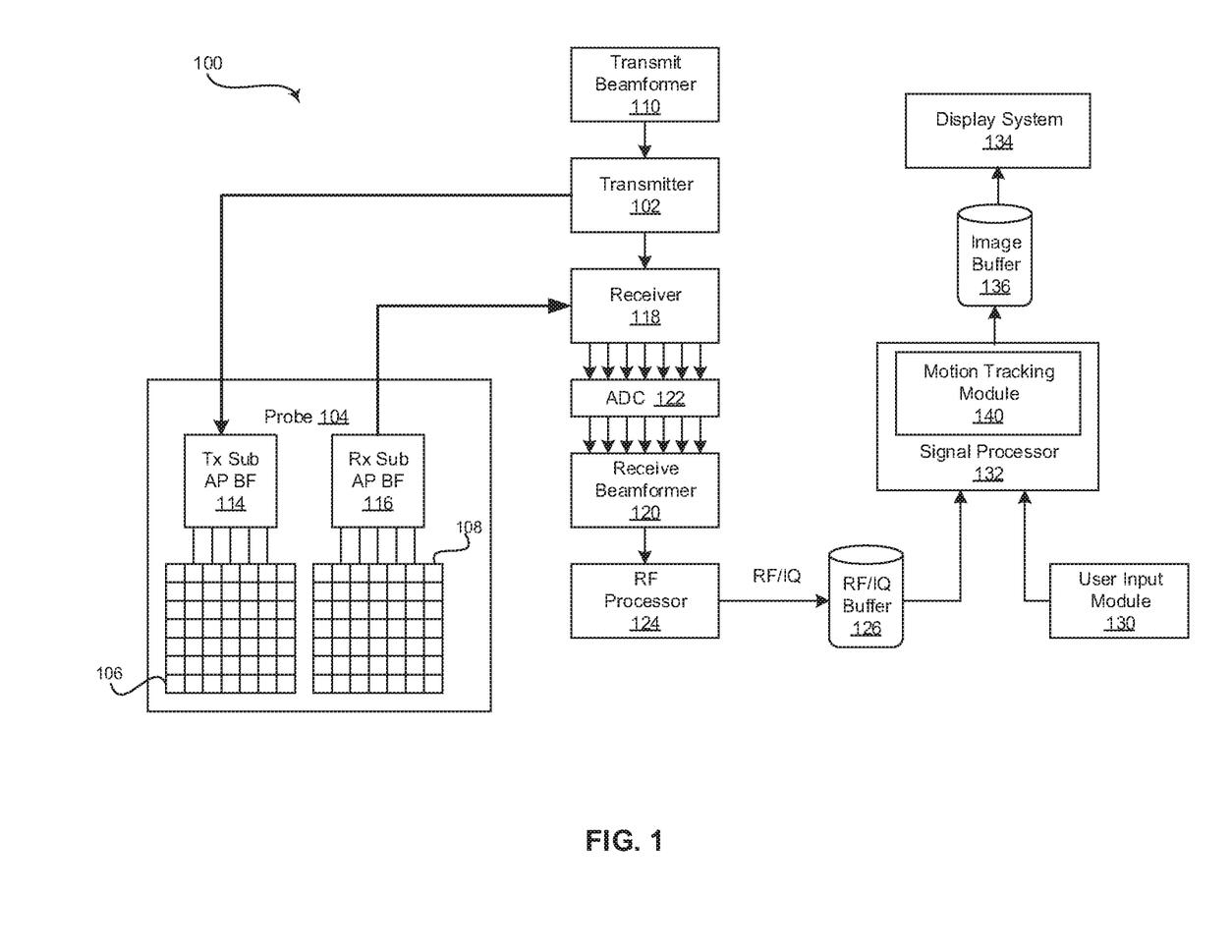
FIG. 1 is a block diagram of an exemplary ultrasound system that is operable to provide enhanced visualization of moving structures with cross-plane two-dimensional ultrasound images, in accordance with various embodiments.

FIG. 1 is a block diagram of an exemplary ultrasound system 100 that is operable to provide enhanced visualization of moving structures 204 with cross-plane two-dimensional ultrasound images 200, 202, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, and a display system 134.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the disclosure is not limited in this regard. Accordingly, in some embodiments, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, surgical instrument data, scan parameters, settings, configuration parameters, change scan mode, select a reference position corresponding to structure in image data, and the like. In an exemplary embodiment, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, and/or the display system 134.

The signal processor 132 may comprise suitable logic, circuitry, interfaces and/or code that may be operable to process ultrasound scan data (i.e., RF signal data or IQ data pairs) for generating cross-plane 2D ultrasound image for presentation on a display system 134. In various embodiments, the cross-plane image data for processing by the signal processor 132 may be acquired simultaneously or consecutively with one ultrasound probe 104. The signal processor 132 is operable to perform one or more processing operations according to a plurality of selectable ultrasound modalities on the acquired ultrasound scan data. In an exemplary embodiment, the signal processor 132 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a motion tracking module 140 that comprises suitable logic, circuitry, interfaces and/or code that may be operable to process cross-plane 2D ultrasound scan data to track a reference position 304 corresponding to a selected structure 204 in a first cross-plane image 200 and to update an acquisition position of a second cross-plane image 202 based on the tracked reference position 304 in the first cross-plane image 200. The motion tracking module 140 may receive an instruction from the user input module 130 for selecting the reference point 304 along a cross-plane intersection line 302 that identifies where the second cross plane image 202 intersects a first cross plane image 200. The cross-plane intersection line 302 may be a reference line overlaid on the first cross plane image 200 presented at an ultrasound image display 300 at the display system 134. The reference point selection 304 along the cross-plane intersection line 302 may by displayed with a marker 304 superimposed on the first cross-plane image 200 presented at an ultrasound image display 300 at the display system 134.

The motion tracking module 140 may continue to evaluate ultrasound scan data as it is continuously acquired to track the selected reference point 304 associated with the moving structure 204. For example, the motion tracking module 140 may apply image detection techniques and/or algorithms to automatically identify the moving structure 204 corresponding with the selected reference point 304 in the first cross-plane image 200. The image detection techniques and/or algorithms may search the image data for structure matching the selected structure 204. The search may be based on the known appearance of the structure at the time of selection and/or the known appearance of the structure as it has been tracked subsequent to the selection.

Additionally and/or alternatively, the search may be based on known positional information at the time the structure was selected and/or the known positional information as the structure has been tracked subsequent to the selection. For example, the image detection techniques and/or algorithms may access information from previous related processed image data or other stored information regarding the appearance and/or the position of the structure 204 associated with the selected reference point 304.

The motion tracking module 140 may automatically shift the selected reference point 304 and the cross-plane intersection line 302 overlaid on the first cross-plane image 200 with the detected movement of the corresponding structure 204. The motion tracking module 140 may dynamically adjust the acquisition parameters corresponding with the position of the second cross-plane image 202 based on the detected movement of the structure 204. In various embodiments, the update of the position of the acquired second cross-plane image 202 occurs substantially in real-time and simultaneously with the shift of the selected reference point 304 and the cross-plane intersection line 302 in the first cross-plane image 200. The cross-plane images 200, 202 may be provided to the image buffer 136 and/or presented at an ultrasound display 300 at the display system 134. In various embodiments, one or both of the cross-plane images 200, 202 may be a thick slice image, which is defined as an image having a thickness from 1 to 50 millimeters. For example, a slice having a defined thickness (also referred to as depth) may be generated by the signal processor 132 projecting the thickness onto a plane based on volume rendering techniques, such as by Volume Contrast Imaging (VCI) or any suitable technique.

Figure 2:
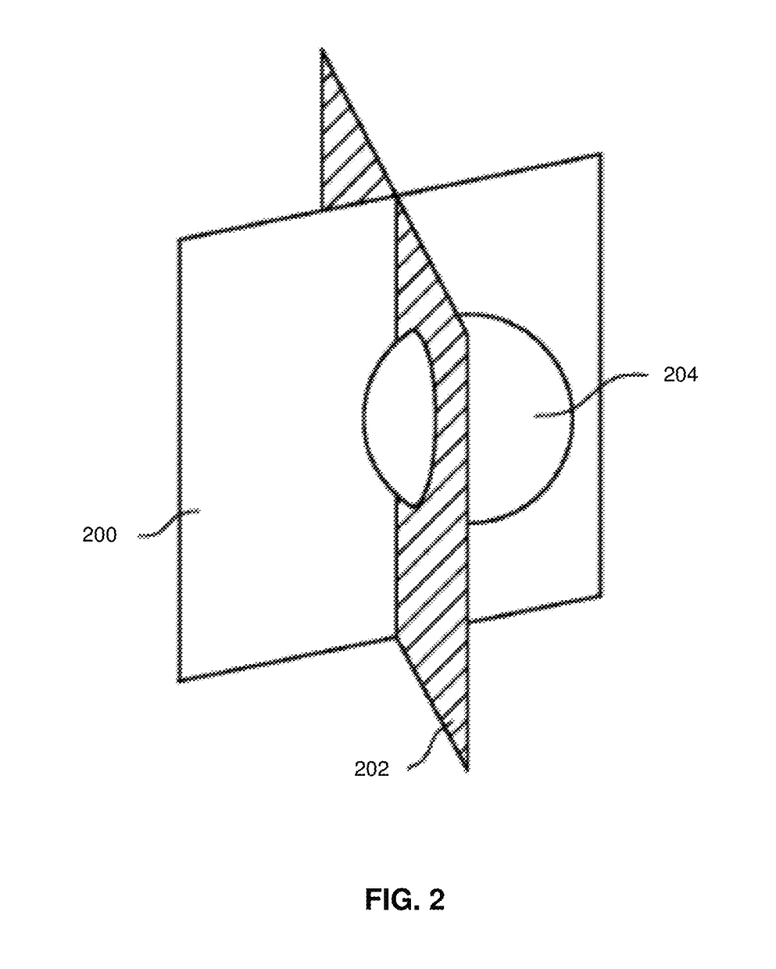
FIG. 2 illustrates an exemplary schematic representation of a first plane and a second plane intersecting a structure, in accordance with various embodiments.

FIG. 2 illustrates an exemplary schematic representation of a first plane 200 and a second plane 202 intersecting a structure 204, in accordance with various embodiments. Referring to FIG. 2, the first 200 and second 202 planes are perpendicular to each other. The structure 204 may be a fetal heart, for example, or any suitable structure. The 2D ultrasound image data acquired of the first plane 200 may be displayed as a first cross-plane image and the 2D ultrasound image data acquired of the second plane 202 may be displayed as a second cross-plane image as described below in reference to FIGS. 3-5, for example.

Figure 3:
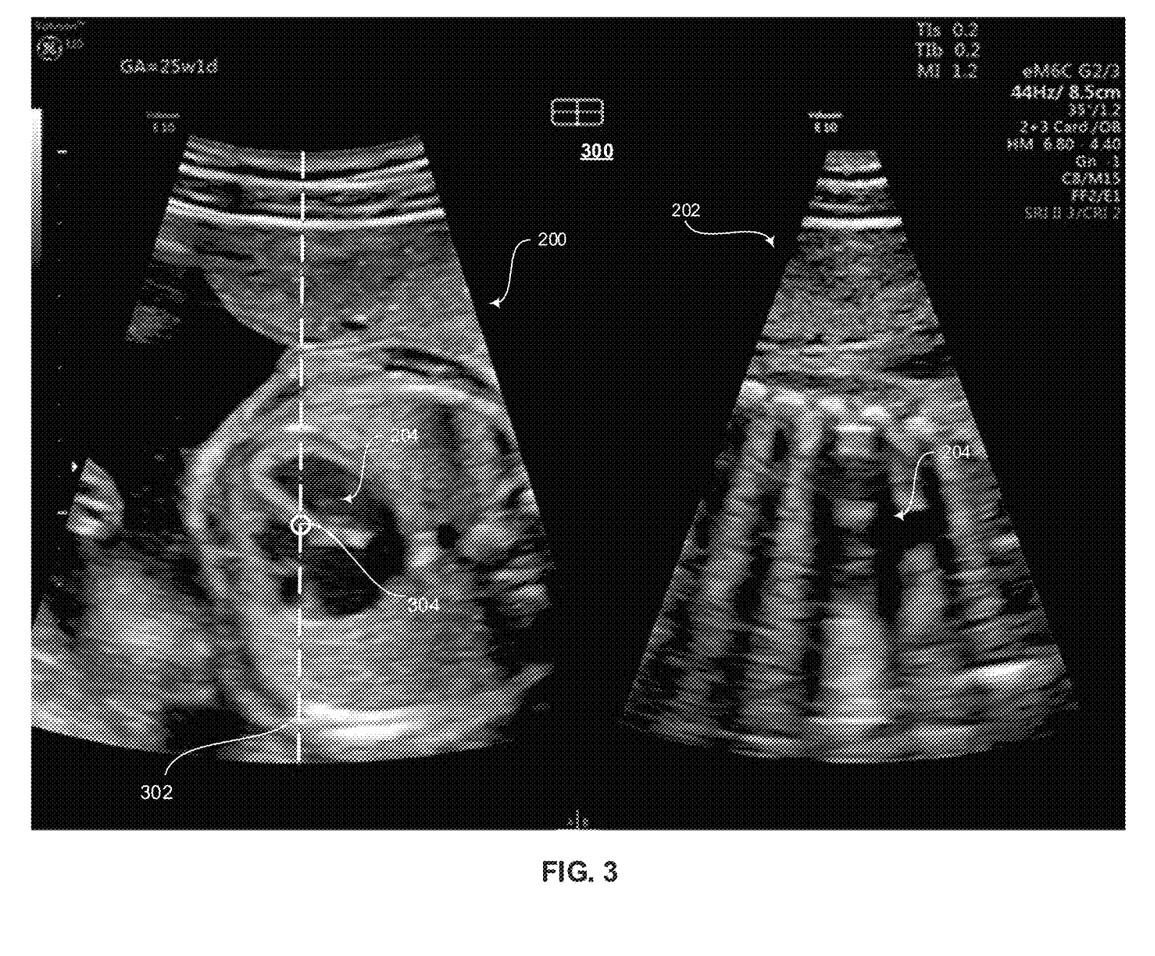
FIG. 3 illustrates exemplary first and second cross-plane ultrasound images, the first cross-plane ultrasound image having a selected reference position along a cross-plane intersection line, in accordance with various embodiments.
Figure 4:
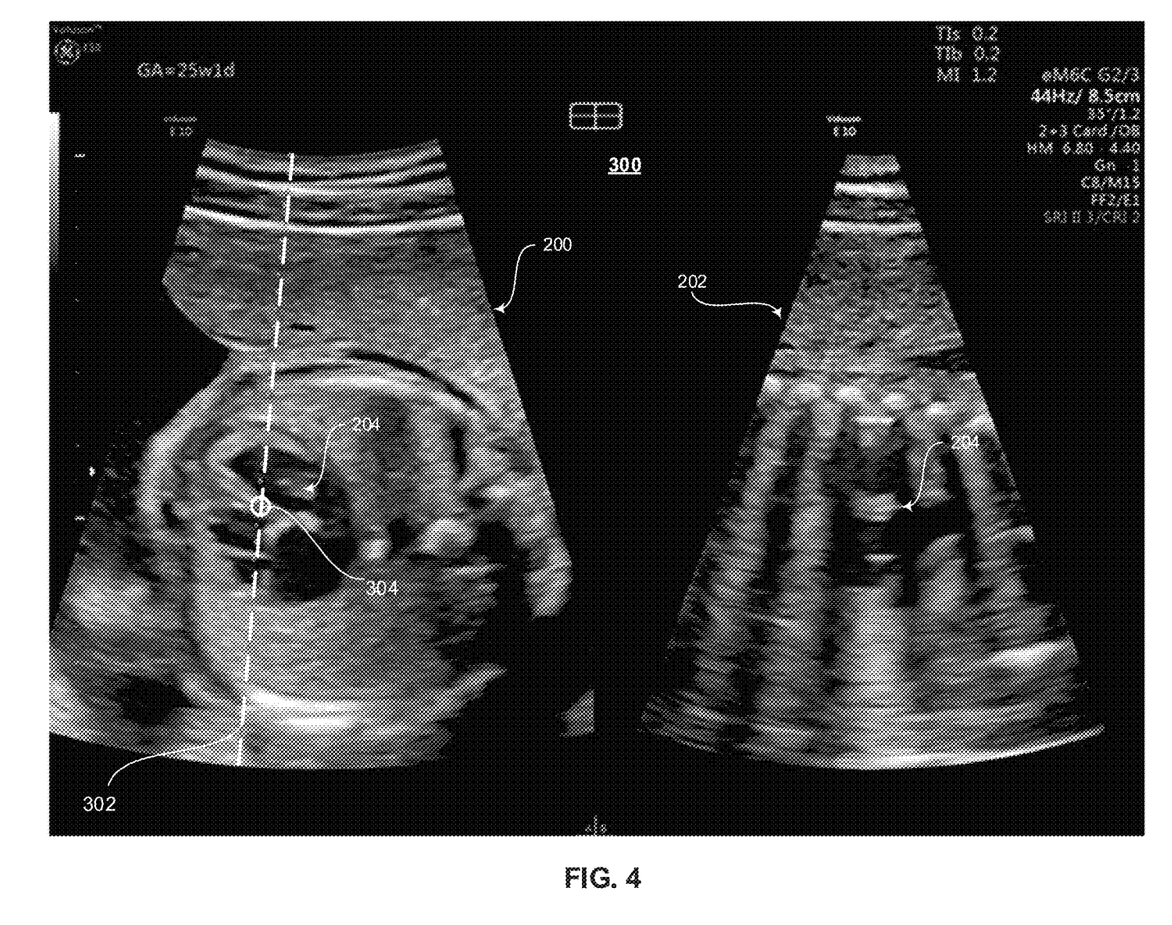
FIG. 4 illustrates exemplary first and second cross-plane ultrasound images, the first cross-plane ultrasound image showing an updated cross-plane intersection line position shifted from FIG. 3 based on the tracked selected reference position, in accordance with various embodiments.
Figure 5:
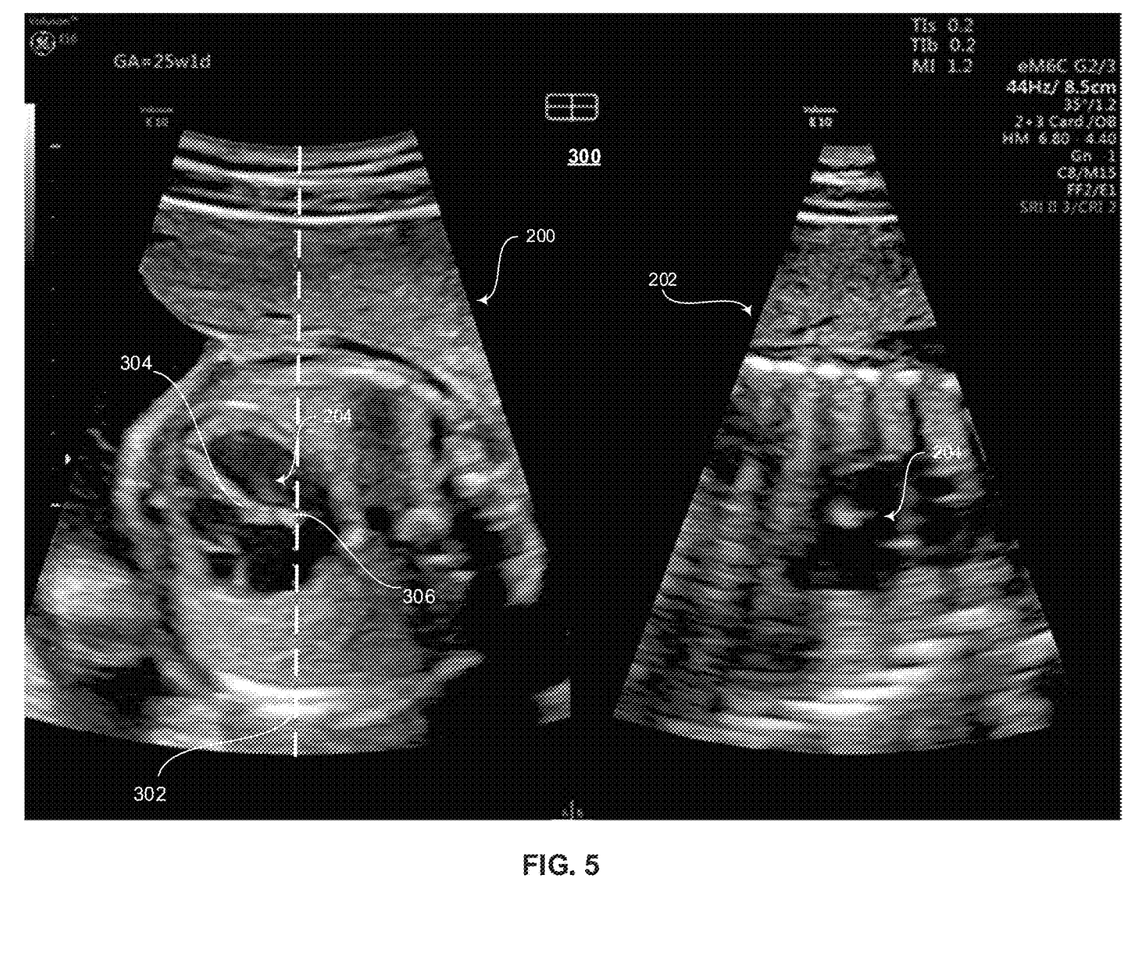
FIG. 5 illustrates exemplary first and second cross-plane ultrasound images without tracking such that the cross-plane intersection line position is unchanged from FIG. 3 despite movement of the imaged structure, in accordance with various embodiments.

FIG. 3 illustrates exemplary first and second cross-plane ultrasound images 200, 202, the first cross-plane ultrasound image 200 having a selected reference position 304 along a cross-plane intersection line 302, in accordance with various embodiments. FIG. 4 illustrates exemplary first and second cross-plane ultrasound images 200, 202, the first cross-plane ultrasound image 200 showing an updated cross-plane intersection line position 302 shifted from FIG. 3 based on the tracked selected reference position 304, in accordance with various embodiments. FIG. 5 illustrates exemplary first and second cross-plane ultrasound images 200, 202 without tracking such that the cross-plane intersection line 302 position is unchanged from FIG. 3 despite movement of the imaged structure 204, in accordance with various embodiments. Referring to FIGS. 3-5, screenshots of an exemplary ultrasound image display 300 that may be presented at a display system 134 comprise a first cross-plane 2D ultrasound image 200 presented adjacent to a second cross-plane 3D ultrasound image 202. The first cross-plane ultrasound image 200 and the second cross-plane ultrasound image 202 may be generated by the signal processor 132 from 2D ultrasound image data acquired simultaneously or consecutively with an ultrasound probe 104. The first cross-plane ultrasound image 200 may be presented with the second cross-plane ultrasound image 202 at the ultrasound image display 300 at the display system 134 and/or may be stored in the image buffer 136. In various embodiments, one or both of the cross-plane images 200, 202 may be a thick slice image, which is defined as an image having a thickness from 1 to 50 millimeters. The cross-plane ultrasound images 200, 202 provide image data of a structure 204 along two different planes. In various embodiments, the two different planes may be perpendicular to each other as illustrated, for example, in FIG. 2. The first cross-plane image 200 may be an A-plane image having a cross-plane reference line 302 superimposed over the image 200. The cross-plane reference line 302 may correspond with the position of the second cross-plane image 202, which may be a B-plane image perpendicular to the A-plane first cross-plane image 200.

In various embodiments, the first cross-plane image 200 may be overlaid with a marker identifying a selected tracked portion 304 of the structure 204. The marker may be a circle, box, arrow, or any suitable shape or identifying mark. An ultrasound operator may mark and/or select a portion 304 of the structure 204 in the first cross-plane image 200 to track such that the acquisition position of the second cross-plane image 202 is automatically updated as the tracked portion 304 of the structure 204 moves. For example, the structure 204 illustrated in FIGS. 3-5 is a fetal heart that may move itself, with movement of the fetus, and/or with movement of the mother, among other things. The selected portion 304 of the fetal heart 204 may be tracked, for example, by a motion tracking module 140 of a signal processor 132 of the ultrasound system 100. The motion tracking module 140 may update the image acquisition parameters for the second cross-plane image 202 such that the ultrasound system 100 continues to acquire the appropriate plane that goes through the selected portion 304 of the structure 204. The motion tracking module 140 may shift the marker of the selected portion 304 of the structure 204 along with the cross-plane reference line 302, as illustrated in FIG. 4, such that the marker and line 302 continuously identify the tracked portion 304 of the structure 204 and the intersecting position of the second cross-plane image 202.

In certain embodiments, the motion tracking module 140 may not perform tracking and may not update the image acquisition parameters for the second cross-plane image 202 if motion tracking is turned off and/or prior to the selection of a tracked portion 304 of the structure 204. For example, comparing FIG. 3 to FIG. 5, if motion tracking is turned off and/or if the portion 304 of the structure 204 in FIG. 3 is not selected, the cross-plane reference line 302 does not shift with the movement of the structure 204 and the second cross-plane image 202 is not updated based on the new position of the portion 304 of the structure 204 as illustrated in FIG. 5. Instead, as shown in FIG. 5, the cross-plane reference line 302 may intersect the structure 204 at a different portion 306 and the second cross-plane image 202 may correspond with the image data associated with the different portion 306 of the structure 204.

Figure 6:
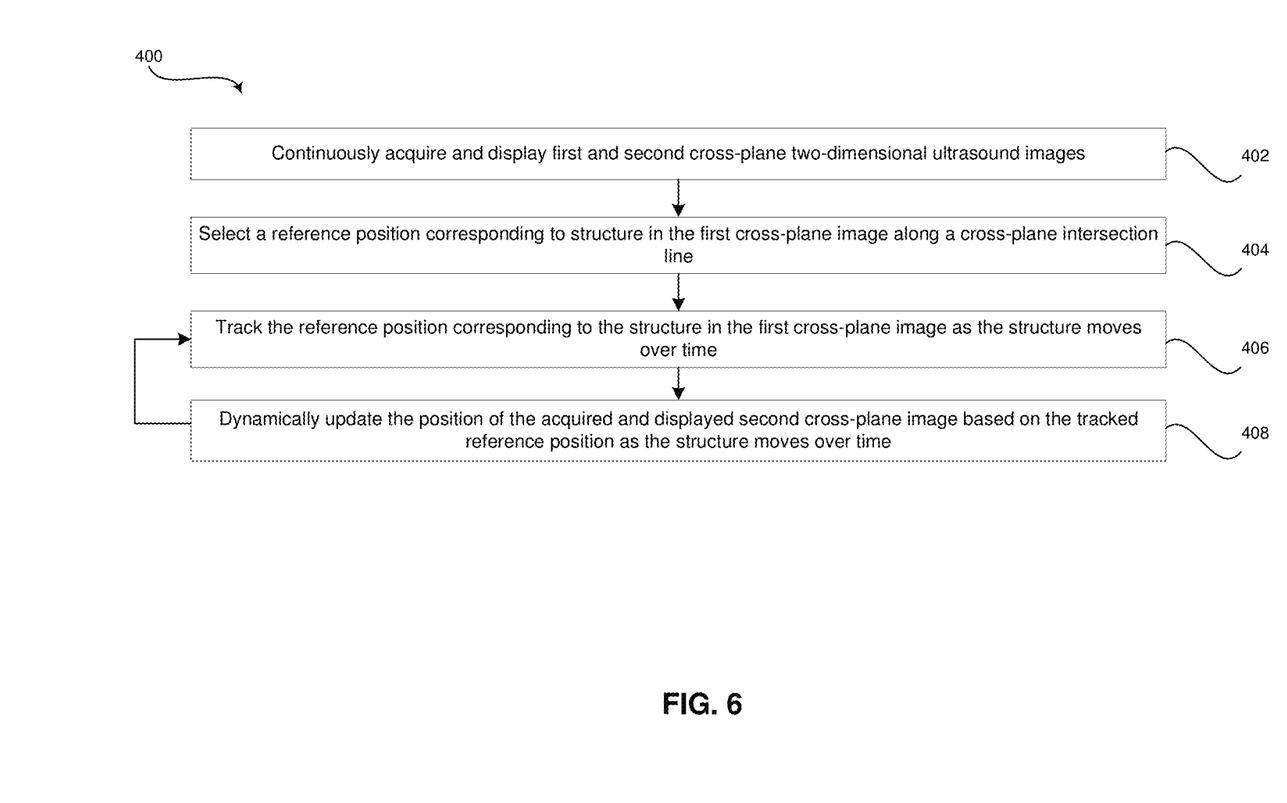
FIG. 6 is a flow chart illustrating exemplary steps that may be utilized for providing enhanced visualization of moving structures with cross-plane two-dimensional ultrasound images, in accordance with various embodiments.

FIG. 6 is a flow chart 400 illustrating exemplary steps 402-408 that may be utilized for providing enhanced visualization of moving structures 204 with cross-plane two-dimensional ultrasound images 200, 202, in accordance with various embodiments. Referring to FIG. 6, there is shown a flow chart 400 comprising exemplary steps 402 through 408. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, a probe 104 of an ultrasound system 100 may continuously acquire cross-plane 2D ultrasound images 200, 202. The ultrasound system 100 may acquire ultrasound data, for example, as described above with regard to FIG. 1. The cross-plane 2D ultrasound image data may comprise a first cross-plane ultrasound image 200 and a second cross-plane ultrasound image 202. The first 200 and second 202 cross-plane ultrasound images may be generated by the signal processor 132 from 2D ultrasound image data acquired simultaneously or consecutively with the ultrasound probe 104. In various embodiments, one or both of the cross-plane images 200, 202 may be a thick slice image. The second cross-plane ultrasound image 202 may be perpendicular to the first cross-plane ultrasound image 200. The first cross-plane ultrasound image 200 may be presented with the second cross-plane ultrasound image 202 at an ultrasound image display 300 of the display system 134 and/or may be stored in the image buffer 136. The ultrasound image display 300 of the display system 134 may simultaneously present the first cross-plane ultrasound image 200 adjacent to the second cross-plane ultrasound image 202. The ultrasound image display 300 may include a cross-plane intersection line 302 superimposed on the first cross-plane image 200 identifying the position of the second perpendicular cross-plane image 202 with reference to the first cross-plane image 200.

At step 404, the motion tracking module 140 of the signal processor 132 may receive a reference position selection 304 corresponding to structure 204 in the first cross-plane image 200 along the cross-plane intersection line 302. For example, the motion tracking module 140 of the signal processor 132 may receive information from a user input module 130 manually identifying the moving structure 204 along the cross-plane intersection line 302 in the first cross-plane ultrasound image 200 to track. In various embodiments, an ultrasound operator may use the user input module 130 to manually position the reference position 304 at a point on the cross-plane intersection line 302. The selected position may be identified by a marker, such as a circle, arrow, box, or any suitable shape or identifying mark. The marker 304 may be superimposed on the first cross-plane image 200 in the ultrasound image display 300 of the display system 134.

At step 406, the motion tracking module 140 of the signal processor 132 may track the reference position 304 corresponding to the structure 204 selected in the first cross-plane image 200 at step 404 as the reference position 304 moves over time. For example, the motion tracking module 140 may apply image detection techniques and/or algorithms to automatically identify the portion 304 of the structure 204 selected at step 404. The image detection techniques and/or algorithms may search the image data for matching structure and/or positions. The search may be based on known structure appearance information and/or positional information. For example, the image detection techniques and/or algorithms may use the initial and/or previously tracked structure position and/or structure appearance characteristic information determined at step 404 or from a previous iteration of step 406 to search for the selected portion 304 of the structure 204 in the current acquired first cross-plane image 200.

At step 408, the motion tracking module 140 of the signal processor 132 may dynamically update the position of the acquired and displayed second cross-plane image 202 based on the tracked reference position 304 as the imaged structure 204 moves over time. For example, the motion tracking module 140 may automatically update the image acquisition parameters for the second cross-plane image 202 such that the ultrasound system 100 continues to acquire the appropriate plane that intersects the selected portion 304 of the structure 204. The motion tracking module 140 may shift the marker of the selected portion 304 of the structure 204 and the cross-plane reference line 302 such that the marker and line 302 presented at the ultrasound image display 300 at the display system 134 continuously identify the tracked portion 304 of the structure 204 and the intersecting position of the second cross-plane image 202. In an exemplary embodiment, steps 406 and 408 are repeated as new cross-plane image data is continuously acquired by the ultrasound probe 104 and analyzed by the motion tracking module 140 of the signal processor 132 for display at the display system 134.

Although the method of FIG. 6 discloses first and second cross-plane images, additional cross-plane images are contemplated. For example, additional reference positions may be selected in the first cross-plane image, each of the additional reference positions corresponding with an additional cross-plane image. In various embodiments, the position of each of the additional cross-plane images may be dynamically updated based on tracking the selected additional reference position in the first cross-plane image as the structure moves over time.

Aspects of the present disclosure provide a method 400 for providing enhanced visualization of moving structures 204 with cross-plane two-dimensional ultrasound images 200, 202. In accordance with various embodiments, the method 400 comprises continuously acquiring 402, by an ultrasound probe 104, a first cross-plane image 200 and a second cross-plane image 202 that intersects the first cross-plane image 200 at a cross-plane intersection line 302 of the first-cross plane image 200. The method 400 comprises receiving 404, by a processor 132, 140, a selection of a reference position 304 in the first cross-plane image 200 along the cross-plane intersection line 302 of the first cross-plane image 200. The selected reference position 304 corresponds with at least a portion of a structure 204 in the first cross-plane image 200. The method 400 comprises tracking 406, by the processor 132, 140, movement of the selected reference position 304 in the first cross-plane image 200 over time. The method 400 comprises updating 408, by the processor 132, 140, an image acquisition position parameter of the second cross-plane image 202 based on the tracked reference position 304 such that the second cross-plane image 202 intersects the first cross-plane image 200 at the tracked reference position 304.

In various embodiments, the method 400 comprises continuously presenting 402 the acquired first cross-plane image 200 and the acquired second-cross plane image 202 simultaneously at a display system 134. In certain embodiments, the cross-plane intersection line 302 is overlaid on the first-cross plane image 200 continuously presented at the display system 134. In a representative embodiment, the method 400 comprises shifting 408 the cross-plane intersection line 302 overlaid on the first-cross plane image 200 to intersect the tracked reference position 304. In various embodiments, a marker corresponding with the reference position 302 is overlaid on the first-cross plane image 200 continuously presented at the display system 134. In certain embodiments, the method 400 comprises shifting 408 the marker overlaid on the first-cross plane image 200 based on the tracking of the movement of the selected reference position 304 in the first cross-plane image 200 over time.

In a representative embodiment, the method 400 comprises continuously acquiring 402, by the ultrasound probe 104, a third cross-plane image that intersects the first cross-plane image 200 at the cross-plane intersection line 302 of the first-cross plane image 200. The method 400 comprises receiving 404, by the processor 132, 140, a selection of an additional reference position 304 in the first cross-plane image 200 along the cross-plane intersection line 302 of the first cross-plane image 200. The selected additional reference position 304 corresponds with at least a portion of the structure 204 in the first cross-plane image 200. The method 400 comprises tracking 406, by the processor 132, 140, movement of the selected additional reference position 304 in the first cross-plane image 200 over time. The method 400 comprises updating 408, by the processor 132, 140, an image acquisition position parameter of the third cross-plane image based on the tracked additional reference position 304 such that the third cross-plane image intersects the first cross-plane image 200 at the tracked additional reference position 304.

In certain embodiments, the first cross-plane image 200 and the second cross-plane image 202 are one or both of B-mode images or color Doppler images. In various embodiments, the second cross-plane image 202 is perpendicular to the first cross-plane image 200. In a representative embodiment, one or both of the first cross-plane image 200 and the second cross-plane image are thick slice images. In certain embodiments, the ultrasound probe 104 comprises a two dimensional (2D) array of piezoelectric elements configured to simultaneously acquire the first cross-plane image 200 and the second cross-plane image 202.

Various embodiments provide a system 100 for providing enhanced visualization of moving structures 204 with cross-plane two-dimensional ultrasound images 200, 202. The system 100 comprises an ultrasound probe 104 configured to continuously acquire a first cross-plane image 200 and a second cross-plane image 202 that intersects the first cross-plane image 200 at a cross-plane intersection line 302 of the first-cross plane image 200. The system 100 comprises a processor 132, 140 configured to receive a selection of a reference position 304 in the first cross-plane image 200 along the cross-plane intersection line 302 of the first cross-plane image 200. The selected reference position 304 corresponds with at least a portion of a structure 204 in the first cross-plane image 200. The processor 132, 140 is configured to track movement of the selected reference position 304 in the first cross-plane image 200 over time. The processor 132, 140 is configured to update an image acquisition position parameter of the second cross-plane image 202 based on the tracked reference position 304 such that the second cross-plane image 202 intersects the first cross-plane image 200 at the tracked reference position 304.

In certain embodiments, the system 100 comprises a user input module 130 configured to provide the selection of the reference position 304 to the processor 132, 140. In a representative embodiment, the system 100 comprises a display system 134 configured to continuously and simultaneously present the acquired first cross-plane image 200 and the acquired second-cross plane image 202. In various embodiments, the processor 132, 140 is configured to superimpose the cross-plane intersection line 302 on the first-cross plane image 200 continuously presented at the display system 134. The processor 132, 140 is configured to shift the cross-plane intersection line 302 to intersect with the tracked reference position 304 based on the movement of the tracked reference position 304 over time. In certain embodiments, the processor 132, 140 is configured to superimpose a marker corresponding with the reference position 304 on the first-cross plane image 200 continuously presented at the display system 134. The processor 132, 140 is configured to shift the marker on the first-cross plane image 200 based on the tracking of the movement of the selected reference position 304 in the first cross-plane image 200 over time.

In a representative embodiment, the ultrasound probe 104 is configured to continuously acquire a third cross-plane image that intersects the first cross-plane image 200 at the cross-plane intersection line 302 of the first-cross plane image 200. In various embodiments, the processor 132, 140 is configured to receive a selection of an additional reference position 304 in the first cross-plane image 200 along the cross-plane intersection line 302 of the first cross-plane image 200. The selected additional reference position 304 corresponds with at least a portion of the structure 204 in the first cross-plane image 200. In certain embodiments, the processor 132, 140 is configured to track movement of the selected additional reference position 304 in the first cross-plane image 200 over time. In a representative embodiment, the processor 132, 140 is configured to update an image acquisition position parameter of the third cross-plane image based on the tracked additional reference position 304 such that the third cross-plane image intersects the first cross-plane image 200 at the tracked additional reference position 304.

In various embodiments, the first cross-plane image 200 and the second cross-plane image 202 are one or both of B-mode images or color Doppler images. In certain embodiments, the second cross-plane image 202 is perpendicular to the first cross-plane image 200. In a representative embodiment, one or both of the first cross-plane image 200 and the second cross-plane image 202 are thick slice images. In various embodiments, the ultrasound probe 104 comprises a two dimensional (2D) array of piezoelectric elements configured to simultaneously acquire the first cross-plane image 200 and the second cross-plane image 204.

Certain embodiments provide a non-transitory computer readable medium having stored thereon, a computer program having at least one code section. The at least one code section is executable by a machine for causing the machine to perform steps. The steps 400 include continuously acquiring 402 a first cross-plane image 200 and a second cross-plane image 202 that intersects the first cross-plane image 200 at a cross-plane intersection line 302 of the first-cross plane image 200. The steps 400 include receiving 404 a selection of a reference position 304 in the first cross-plane image 200 along the cross-plane intersection line 302 of the first cross-plane image 200. The selected reference position 304 corresponds with at least a portion of a structure 204 in the first cross-plane image 200. The steps 400 include tracking 406 movement of the selected reference position 304 in the first cross-plane image 200 over time. The steps 400 include updating 408 an image acquisition position parameter of the second cross-plane image 202 based on the tracked reference position 304 such that the second cross-plane image 202 intersects the first cross-plane image 200 at the tracked reference position 304.

In various embodiments, the steps 400 include continuously displaying 402 the acquired first cross-plane image 200 and the acquired second-cross plane image 202 simultaneously. The cross-plane intersection line 302 is overlaid on the continuously displayed first-cross plane image 200 and shifted over time based on the movement of the tracked reference position 304 to intersect the tracked reference position 302. A marker corresponding with the reference position 304 is overlaid on the continuously displayed first-cross plane image 200 and shifted on the first-cross plane image 200 based on the tracking of the movement of the selected reference position 304 in the first cross-plane image 200 over time. In certain embodiments, the first cross-plane image 200 and the second cross-plane image 202 are one or both of B-mode images or color Doppler images. In a representative embodiment, the second cross-plane image 202 is perpendicular to the first cross-plane image 200. In various embodiments, the first cross-plane image 200 and the second cross-plane image 202 are simultaneously acquired by an ultrasound probe 104 comprising a two dimensional (2D) array of piezoelectric elements. In various embodiments, one or both of the first cross-plane image 200 and the second cross-plane image 202 are thick slice images.

In a representative embodiment, the steps 400 include continuously acquiring 402 a third cross-plane image that intersects the first cross-plane image 200 at the cross-plane intersection line 302 of the first-cross plane image 200. In various embodiments, the steps 400 include receiving 404 a selection of an additional reference position 304 in the first cross-plane image 200 along the cross-plane intersection line 302 of the first cross-plane image 200. The selected additional reference position 304 corresponds with at least a portion of the structure 204 in the first cross-plane image 200. In certain embodiments, the steps 400 include tracking 406 movement of the selected additional reference position 304 in the first cross-plane image 200 over time. In a representative embodiment, the steps 400 include updating 408 an image acquisition position parameter of the third cross-plane image based on the tracked additional reference position 304 such that the third cross-plane image intersects the first cross-plane image 200 at the tracked additional reference position 304.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the disclosure may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing enhanced visualization of moving structures with cross-plane two-dimensional ultrasound images.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

The present disclosure may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
continuously acquiring, by an ultrasound probe, a first cross-plane image and a second cross-plane image that intersects the first cross-plane image at a cross-plane intersection line of the first cross-plane image;
continuously presenting the acquired first cross-plane image and the acquired second cross-plane image simultaneously at a display system, wherein the cross-plane intersection line is overlaid on the first cross-plane image continuously presented at the display system;
receiving, by a processor, a user selection of a reference position at a point on the cross-plane intersection line of the first cross-plane image, wherein the selected reference position corresponds with at least a portion of a structure in the first cross-plane image, and wherein a marker corresponding with the reference position is overlaid on the first cross-plane image continuously presented at the display system;
tracking, by the processor, movement of the selected reference position in the first cross-plane image over time;
updating, by the processor, an image acquisition position parameter of the second cross-plane image based on the tracked reference position such that the second cross-plane image intersects the first cross-plane image at the tracked reference position; and
simultaneously shifting, by the processor, the cross-plane intersection line with the marker overlaid on the first cross-plane image based on the tracking of the movement of the selected reference position in the first cross-plane image over time.

2. The method according to claim 1, comprising:
continuously acquiring, by the ultrasound probe, a third cross-plane image that intersects the first cross-plane image at the cross-plane intersection line of the first cross-plane image;
receiving, by the processor, a selection of an additional reference position in the first cross-plane image along the cross-plane intersection line of the first cross-plane image, wherein the selected additional reference position corresponds with at least a portion of the structure in the first cross-plane image;
tracking, by the processor, movement of the selected additional reference position in the first cross-plane image over time; and
updating, by the processor, an image acquisition position parameter of the third cross-plane image based on the tracked additional reference position such that the third cross-plane image intersects the first cross-plane image at the tracked additional reference position.

3. The method according to claim 1, wherein one or more of:
the first cross-plane image and the second cross-plane image are one or both of B-mode images or color Doppler images,
the second cross-plane image is perpendicular to the first cross-plane image, and
one or both of the first cross-plane image and the second cross-plane image are thick slice images.

4. The method according to claim 1, wherein the ultrasound probe comprises a two dimensional (2D) array of piezoelectric elements configured to simultaneously acquire the first cross-plane image and the second cross-plane image.

5. A system comprising:
an ultrasound probe configured to continuously acquire a first cross-plane image and a second cross-plane image that intersects the first cross-plane image at a cross-plane intersection line of the first cross-plane image;
a display system configured to continuously and simultaneously present the acquired first cross-plane image and the acquired second cross-plane image; and
a processor configured to:
superimpose the cross-plane intersection line on the first cross-plane image continuously presented at the display system;
receive a user selection of a reference position at a point on the cross-plane intersection line of the first cross-plane image, wherein the selected reference position corresponds with at least a portion of a structure in the first cross-plane image;
superimpose a marker corresponding with the reference position on the first cross-plane image continuously presented at the display system;
track movement of the selected reference position in the first cross-plane image over time;
update an image acquisition position parameter of the second cross-plane image based on the tracked reference position such that the second cross-plane image intersects the first cross-plane image at the tracked reference position; and
simultaneously shift the cross-plane intersection line with the marker superimposed on the first cross-plane image based on the movement of the tracked reference position over time.

6. The system according to claim 5, wherein:
the ultrasound probe is configured to continuously acquire a third cross-plane image that intersects the first cross-plane image at the cross-plane intersection line of the first cross-plane image; and the processor is configured to:

receive a selection of an additional reference position in the first cross-plane image along the cross-plane intersection line of the first cross-plane image, wherein the selected additional reference position corresponds with at least a portion of the structure in the first cross-plane image;

track movement of the selected additional reference position in the first cross-plane image over time; and update an image acquisition position parameter of the third cross-plane image based on the tracked additional reference position such that the third cross-plane image intersects the first cross-plane image at the tracked additional reference position.

7. The system according to claim 5, wherein one or more of:

the first cross-plane image and the second cross-plane image are one or both of B-mode images or color Doppler images, the second cross-plane image is perpendicular to the first cross-plane image, one or both of the first cross-plane image and the second cross-plane image are thick slice images, and the ultrasound probe comprises a two dimensional (2D) array of piezoelectric elements configured to simultaneously acquire the first cross-plane image and the second cross-plane image.

8. A non-transitory computer readable medium having stored thereon, a computer program having at least one code section, the at least one code section being executable by a machine for causing the machine to perform steps comprising:

continuously acquiring a first cross-plane image and a second cross-plane image that intersects the first cross-plane image at a cross-plane intersection line of the first cross-plane image;

continuously presenting the acquired first cross-plane image and the acquired second cross-plane image simultaneously at a display system, wherein the cross-plane intersection line is overlaid on the first cross-plane image continuously presented at the display system;

receiving a user selection of a reference position at a point on the cross-plane intersection line of the first cross-plane image, wherein the selected reference position corresponds with at least a portion of a structure in the first cross-plane image, and wherein a marker corresponding with the reference position is overlaid on the first cross-plane image continuously presented at the display system;

tracking movement of the selected reference position in the first cross-plane image over time;

updating an image acquisition position parameter of the second cross-plane image based on the tracked reference position such that the second cross-plane image intersects the first cross-plane image at the tracked reference position; and simultaneously shifting the cross-plane intersection line with the marker overlaid on the first cross-plane image based on the tracking of the movement of the selected reference position in the first cross-plane image over time.

9. The non-transitory computer readable medium according to claim 8, wherein one or both of:

the first cross-plane image and the second cross-plane image are one or both of B-mode images or color Doppler images, and the second cross-plane image is perpendicular to the first cross-plane image.

10. The non-transitory computer readable medium according to claim 8, wherein one or both of:

the first cross-plane image and the second cross-plane image are simultaneously acquired by an ultrasound probe comprising a two dimensional (2D) array of piezoelectric elements, and one or both of the first cross-plane image and the second cross-plane image are thick slice images.

11. The non-transitory computer readable medium according to claim 8, comprising:

continuously acquiring a third cross-plane image that intersects the first cross-plane image at the cross-plane intersection line of the first cross-plane image;

receiving a selection of an additional reference position in the first cross-plane image along the cross-plane intersection line of the first cross-plane image, wherein the selected additional reference position corresponds with at least a portion of the structure in the first cross-plane image;

tracking movement of the selected additional reference position in the first cross-plane image over time; and updating an image acquisition position parameter of the third cross-plane image based on the tracked additional reference position such that the third cross-plane image intersects the first cross-plane image at the tracked additional reference position.

* * * * *